United States Patent [19]

Lang et al.

[11] Patent Number: 4,931,271
[45] Date of Patent: Jun. 5, 1990

[54] COSMETIC COMPOSTIONS BASED UPON N-HYDROXYBUTYL-CHITOSANS, N-HYDROXYBUTYL-CHITOSANS AS WELL AS PROCESSES FOR THE PRODUCTION THEREOF

[75] Inventors: Günther Lang, Reinheim; Eugen Konrad, Darmstadt; Harald Wendel, Ober-Ramstadt; Gerhard Maresch; Hans-Rudi Lenz, both of Darmstadt, all of Fed. Rep. of Germany

[73] Assignee: Wella Aktiengesellschaft, Darmstadt, Fed. Rep. of Germany

[21] Appl. No.: 134,779
[22] PCT Filed: Apr. 16, 1987
[86] PCT No.: PCT/EP87/00207
  § 371 Date: Nov. 18, 1987
  § 102(e) Date: Nov. 18, 1987
[87] PCT Pub. No.: WO87/06461
  PCT Pub. Date: Nov. 5, 1987

[30] Foreign Application Priority Data

Apr. 30, 1986 [DE] Fed. Rep. of Germany ....... 3614697

[51] Int. Cl.$^5$ .......................... A61K 7/06; A61K 7/08; A61K 7/13; C08B 37/08
[52] U.S. Cl. ..................................... 424/47; 536/20; 424/70; 8/405; 8/406; 132/208
[58] Field of Search ....................... 536/20, 18.5, 55.3; 424/70, 47; 8/405, 406; 132/7

[56] References Cited

U.S. PATENT DOCUMENTS

| 3,914,413 | 10/1975 | Balassa | 514/55 |
| 4,376,199 | 3/1983 | Koshugi | 536/20 |
| 4,424,346 | 1/1984 | Hall et al. | 536/20 |
| 4,528,283 | 7/1985 | Lang et al. | 536/20 |
| 4,765,976 | 8/1988 | Grollier et al. | 424/70 |
| 4,780,310 | 10/1988 | Lang et al. | 536/20 |

FOREIGN PATENT DOCUMENTS 0028126 5/1981 European Pat. Off. .
0193736 9/1986 European Pat. Off. .

OTHER PUBLICATIONS

Matsuda et al.; Chemical Abstracts 85:83105s, (1976).

Primary Examiner—Ronald W. Griffin
Assistant Examiner—Nancy S. Carson
Attorney, Agent, or Firm—Michael J. Striker

[57] ABSTRACT

The invention is directed to cosmetic compositions for the treatment of hair or skin characterized in that they contain new N-hydroxybutyl-chitosans, or their salts, consisting of
(a) 4 to 40 mole percent monomer units of the formula (I)

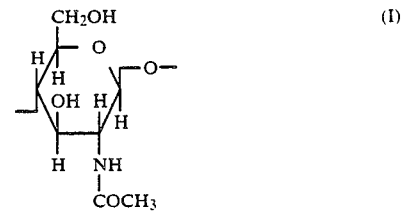

and
(b) 60 to 96 mole percent monomer units of the formula (II)

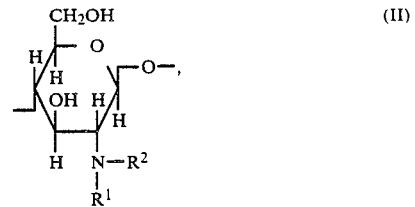

wherein $R^1$ and $R^2$ are identical or different and designate hydrogen or the group

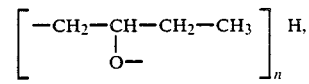

with n being equal to an integer from 1 to 5, provided that $R^1$ and $R^2$ are not simultaneously hydrogen in at least 50 percent of the units of formula (II). In addition, it is directed to new N-hydroxybutyl-chitosans and their salts and a process for producing these new compounds from butylene oxide and chitosan.

14 Claims, No Drawings

COSMETIC COMPOSTIONS BASED UPON N-HYDROXYBUTYL-CHITOSANS, N-HYDROXYBUTYL-CHITOSANS AS WELL AS PROCESSES FOR THE PRODUCTION THEREOF

The invention is directed to cosmetic compositions for treating hair or skin, containing new macromolecular compounds derived from chitosan, which are used in a suitable cosmetic base.

The invention is directed, in addition, to new N-hydroxybutyl-chitosans and to a process for the production thereof.

The use of cation-active polymers, particularly polymers having quaternary ammonium groups, as conditioning agents in cosmetic compositions, particularly for the treatment of hair, is already known. Because of a reciprocal action between their ammonium groups and the anionic groups of the hair, the cation-active polymers have a great affinity with keratin fibers.

It has been established that the use of such cation-active polymers in such cosmetic compositions results in numerous advantages: the disentanglement of hair and its treatment are facilitated; furthermore, the hair obtains springiness and luster. However, because of this affinity with keratin, these polymers tend to collect on the hair after repeated use so that the hair becomes heavier, which is ultimately undesirable.

In addition, there are problems with synthetic polymers due to the physiological effect of monomer traces which may possible be present and which are difficult to remove from the polymer.

Attempts have already been made to overcome the aforementioned disadvantages in that water-soluble salts of chitosan, a polyglucose amine which is producible by means of deacetylation of chitin, are used in such cosmetic compositions. In this context, reference is made to the Applicant's European Patent No. 0 002 506 and the Applicant's German Patent No. 26 27 419.

Just as in the multiplicity of cation-active polymers with quaternary grouping, chitosan also frequently has the disadvantage that its compatibility with the anion-active surface-active agents which are usually used in cosmetic compositions for treating hair, particularly in shampoos, is poor. Therefore, it is necessary to put the chitosan to use in separate treatments, namely before and/or after the shampooing.

Moreover, the chitosan proves to be practically insoluble in neutral and alkaline media, so that it is impossible to use it, for example, in alkaline permanent wave compositions or hair dye compositions.

By using glycidyl chitosans, according to the Applicant's DE-OS 32 23 423, instead of chitosan salts, the aforementioned disadvantages can be avoided. However, the reaction of chitosan with glycide is very cost-intensive, since glycide is an expensive raw material which is not producible on an industrial scale.

However, the aforementioned chitosans, or chitosan derivatives, have a further disadvantage, since they are scarcely, or not at all, soluble in organic solvents. It would therefore be a great advantage if such derivatives were soluble in organic solvents so as to enlarge, accordingly, the possibilities of use in cosmetic compositions.

Therefore, it is the object of the invention to provide inexpensive compositions with which the aforementioned disadvantages can be avoided.

In continuing investigations with chitosan and the compounds derived therefrom, it has now been found that certain chitosan derivatives, especially N-hydroxybutyl chitosans, also do not have the aforementioned disadvantages and can be obtained, in addition, in a substantially less expensive manner than the previously known glycidyl chitosans. Moreover, such derivatives are also soluble in organic solvents, such as ethanol and isopropanol, for example, and thus enable the production of anhydrous, e.g. alcoholic, solutions.

In contrast to the synthetic polymers with final residual monomer contents, these N-hydroxybutyl-chitosans are harmless physiologically and are biologically degradable. Because of their film characteristics, their solubility in organic solvents, and their thickening action and compatibility with anionic surfactants, they can be used not only as new, interesting raw materials for cosmetics, but also in pharmaceutics, as flocculants and thickeners in the treatment of waste water, as finishing and sizing agents in the textile industry, and in paper manufacturing.

Accordingly, cosmetic compositions for the treatment of hair or skin, which are distinguished by surprisingly advantageous characteristics, can be produced with N-hydroxybutyl chitosans or their salts with organic or inorganic acids and are characterized in that they contain, in a suitable cosmetic base, an N-hydroxybutyl-chitosan, consisting of (a) 4 to 40 mole percent monomer units of the formula (I)

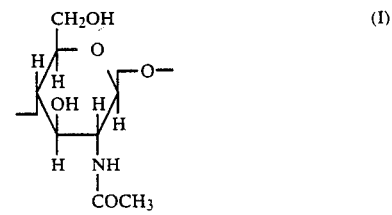

and (b) 60 to 96 mole percent monomer units of the formula (II)

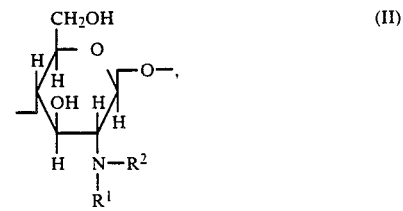

or its soluble salts with organic or inorganic acids, wherein $R^1$ and $R^2$ are identical or different and designate hydrogen or the radical of the formula (III):

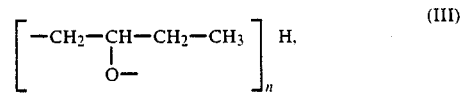

with n being equal to an integer from 1 to 5, provided that $R^1$ and $R^2$ do not simultaneously represent hydrogen in at least 50 percent of the units of formula (II).

The compositions containing the N-hydroxybutyl-chitosan, according to the invention, are generally suitable for the treatment of skin and/or hair. They can be provided as hair and/or body washing agents, tinting shampoos, hair creams, hair lotions, hair drying lotions, compositions for setting hairstyles, washing lotions, hair treatments, compositions for preventing dandruff, compositions for permanently shaping the hair, compositions for dyeing or removing dye from the hair, compositions for application before or after dyeing the hair, and as cosmetic compositions for the care, protection, or cleansing of the skin, such as face lotions, shaving lotions, moisturizing creams, cold creams, body lotions, sun screens or also makeup preparations such as cosmetic creams and rouges.

The content of N-hydroxybutyl-chitosan in the cosmetic compositions according to the invention is advisably 0.05 to 10 percent by weight, preferably 0.05 to 3.0 percent by weight.

For producing a cosmetic base, the cosmetic compositions, according to the present invention, in addition to the new active ingredient, N-hydroxybutylchitosan, can contain all those components conventionally used in hair and skin treatment compositions, particularly anionic, cationic, amphoteric, zwitterionic or nonionic surface-active surfactants, foam synergists, stabilizing agents, sequestering agents, pigments, thickeners, emulsifiers, buffer materials, preservatives, dyestuffs, perfume oils, known cosmetic polymers such as anionic, nonionic, cationic or amphoteric polymers, natural materials, cosmetic oils, fatty alcohols, waxes, foam stabilizers, active ingredients against dandruff, reducing agents and propellants.

The cosmetic compositions, according to the invention, preferably have a pH value of 2 to 11 and can be provided in the form of aqueous, alcoholic or aqueous-alcoholic preparations, particularly as solutions, creams, gels, dispersions or as emulsions.

It is likewise possible to dispense these compositions from pressurized containers as aerosol spray (for example, aerosol hair spray) or aerosol foam with the aid of an atomizer or other suitable spraying devices or in a mixture with conventional liquified propellants under pressure.

The cosmetic compositions, according to the invention, are preferably compositions for setting the hairstyle, such as liquid hair setting compositions or hair sprays. The latter are usually aqueous, alcoholic or aqueous-alcoholic solutions which are characterized through a content of N-hydroxybutyl-chitosan consisting of units of the aforementioned formulas (I) and (II) or its soluble salts with organic or inorganic acids. The N-hydroxybutylchitosan itself can be used as a film-forming or setting resin; however, additional film-forming natural or synthetic cosmetic polymers can also be contained in the hair setting compositions according to the invention. Shellac, alginates, gelatines, pectins and cellulose derivatives, for example, come under consideration as natural polymers. Use is made of the following synthetic polymers, for example: polyvinylpyrrolidone, polyvinyl acetate, polyacrylic compounds such as acrylic acid or methacrylic acid polymers, basic polymers of esters from acrylic acid or methacrylic acid with amino alcohols, or the salts or quaternization products of these basic polymers, polyacrylnitrile and copolymers or terpolymers of such compounds, for example, polyvinylpyrrolidonevinylacetate.

The compositions then have a pH value between 6 and 8 in particular. Such compositions for setting the hairstyle usually contain the film-forming polymers in a total quantity of approximately 0.05 to 3.0 percent by weight. If the compositions contain other film-forming polymers aside from the N-hydroxybutyl-chitosan from units of the aforementioned formulas (I) and (II), the content of N-hydroxybutyl-chitosan is correspondingly reduced.

The lower alcohols with 1 to 4 carbon atoms which are usually used for cosmetic purposes, ethanol and isopropanol, for example, are particularly taken into consideration as alcohols.

If the hair setting compositions are in the form of aerosol preparations which are sprayed from a pressurized container, their cosmetic base contains approximately 10 to 60 percent by weight of a propellant. Chlorofluoroalkanes, such as $CCl_3F$, $CCl_2F_2$, $C_2Cl_3F_3$, $(CCl_2F)_2$, $CHCl_2F$ and $(CClF_2)_2$, readily volatile hydrocarbons such as n-butane and n-propane, or also dimethyl ether, carbon dioxide, dinitrogen monoxide, nitrogen, methylene chloride and 1,1,1-trichloroethane can be used as propellants.

The hair setting compositions, according to the invention, can also contain the additives usually used for such compositions, such as perfume oils, bactericides or fungicides, substances for facilitating combing and modifiers such as silicone oil or emollients such as isopropyl myristate, phthalic acid diethyl ester and diethyl stearate.

The hair setting compositions, according to the invention, can possibly dye or tint the hair simultaneously by means of a content of cosmetic dyestuffs. Such preparations are known commercially as dyeing or tinting strengtheners, etc. They contain known cosmetic dyestuffs which are absorbed directly into the hair and are also conventionally used in hair strengtheners, such as aromatic nitro dyestuffs (for example, 1,4-diamino-2-nitrobenzene, picramic acid, 1-hydroxy-2-amino-4-nitrobenzene, and 1,4-bis-[(2-hydroxyethyl)-amino]-2-nitro-5-chlorobenzene), azo dyestuffs (for example, C.I. 14 805 Acid Brown 4), anthraquinone dyestuffs (for example, C.I. 61 105 Disperse Violet 4) and triphenylmethane dyes (for example, C.I. 42 535 Basic Violet 1), wherein the dyestuffs of these classes can have an acidic, nonionogenic or basic character, depending on their type of substituents. Their total concentration in these preparations is usually approximately 0.01 to 2.0 percent by weight.

The hair setting compositions, according to the invention, have a particularly good combing ability and a good feel of the hair in the wet state and a particularly pleasant feel of the hair in the dry state, with a setting of the hair which is equally as good as conventional compositions.

In addition, the compositions, according to the invention, can be hair washing compositions. They are then provided in the form of aqueous solutions or emulsions and, in addition to the N-hydroxybutyl-chitosan, will contain at least one anionic, cationic, nonionic or amphoteric surfactant.

In these hair washing compositions, the concentration of the surfactant generally amounts to approximately 3 to 50 percent by weight, preferably 3 to 20 percent by weight, wherein the pH value is generally between 3 and 9, preferably between 4 and 7.

The compositions, according to the invention, which are in the form of hair washing compositions, generally contain various additives, particularly perfumes, preservatives, thickeners, foam stabilizers, buffer substances, cosmetic resins, pigments, and dyestuffs.

Among the foam stabilizers are the fatty amides and particularly the mono- or diethanolamides of coconut fatty acids, lauryl- or oleic acid-monoethanolamide or diethanolamide, which are advisably used in quantities of 1 to 10 and preferably from 1 to 3 percent by weight.

Among the thickeners to be considered are particularly acrylic polymers and cellulose derivatives, such as carboxymethyl cellulose, hydroxypropyl methyl cellulose and hydroxyethyl cellulose. The thickeners are generally contained in a proportion of 0.1 to 5 percent by weight.

The following may be mentioned by way of example as surfactants or surface-active agents which are used in combination with the new N-hydroxybutyl-chitosans:

(a) the anionic surface-active agents such as the alkali-, alkaline earth-, ammonium- or alkanol amine salts of alkane sulfonates, alkyl sulfates and alkylether sulfates, $C_{12}$ to $C_{18}$-alkyl- and particularly $C_{12}$ to $C_{14}$-alkyl sulfate sodium salts or -triethanolamine salts, sodium- or triethanol amine salts of lauryl- or tetradecylether sulfates, disodium salt of the sulfosuccinic semiester of alkanol amides, the soaps and the polyether carboxylic acids;

(b) the nonionic surface-active agents such as ethoxylated fatty alcohols with 12 to 18 carbon atoms, for example with up to 40 moles ethylene oxide per mole of fatty alcohol ethoxylated lauryl-, tetradecyl-, cetyl-, oleyl-, and stearyl alcohols, alone or in combination; the fatty alcohols of ethoxylated lanolin or ethoxylated lanolin; polyglycol ethers of saturated or unsaturated fatty alcohols and alkylphenols with 8 to 30 carbon atoms in the alkyl radical and 1 to 10 glyceryl units in the molecule; fatty acid alkanol amides and ethoxylated sorbitan fatty acid ester;

(c) the cationic surface-active agents such as dilauryldimethyl ammonium chloride, the chlorides or bromides of alkyl dimethylbenzyl ammonium, the alkyl trimethyl ammonium salts, for example, cetyl trimethyl ammonium chloride or -bromide, alkyl dimethylhydroxyethyl ammonium chlorides or bromides, dialkyl dimethyl ammonium chlorides or -bromides, alkylpyridinium salts, for example, lauryl- or cetylpyridinium chloride, alkyl amide ethyl trimethyl ammonium ether sulfates, compounds with a cationic character such as amino oxides, for example, alkyl dimethyl amino oxides or alkyl aminoethyldimethylaminooxides;

(d) the amphoteric or zwitterionic surface-active agents such as the carboxyl derivatives of imidazole, N-alkyl betaines, N-alkyl amido betaines, N-alkyl sulfobetaines, N-alkyl amino propionates, alkyl dimethyl ammonium acetates, $C_{12}$ to $C_{18}$-alkyl dimethyl carboxymethyl ammonium salts and fatty acid alkyl amido betaines, for example dimethylcarboxymethylene propylene amido stearate betaine.

The cosmetic compositions according to the invention can also be creams or lotions for use as hair treatment or skin care compositions. Then they are mostly in the form of oil-in-water or water-in-oil emulsions or suspensions and, in addition to the new N-hydroxybutyl-chitosans, also contain cationic, nonionogenic, amphoteric or anionic emulsifiers, as well as fatty alcohols, fatty acid esters or amides as components of the oil phase, in addition to perfume oils, petrolatum, wool fat alcohol, or solid or liquid paraffins.

If the compositions, according to the invention, are hair tinting or hair dyeing compositions, they are preferably likewise in the form of creams or lotions and contain, in addition, conventional hair dyestuffs from the group of aromatic nitro dyes, azo dyes, anthraquinone dyes, triphenylmethane dyes or oxidizing dyes, such as resorcinol and aromatic diamines or aminophenols. Moreover, these compositions can possibly contain alkalizing compositions, antioxidants and other cosmetic additions and auxiliary materials which are conventional in such compositions.

The compositions, according to the invention, can also be permanent shaping compositions or styling compositions for hair. Then, in addition to the aforementioned N-hydroxybutyl-chitosans, they contain reducing agents such as thioglycolic acid, thiolactic acid and ammonium sulfite, or oxidizing agents such as hydrogen peroxide or sodium bromate, and possibly alkalizing agents or peroxide stabilizers, for example, phosphoric acid, and other cosmetic auxiliary materials and additives such as perfume oils, fragrant materials, grooming materials and dyestuffs.

As already mentioned, the cosmetic compositions, according to the invention, can also be used for the treatment of skin.

These cosmetic compositions actually facilitate the moistening of the skin, prevent the skin from drying out and give the skin an outstanding softness in feel.

The cosmetic compositions for this purpose, according to the invention, preferably are provided in the form of creams, gels, emulsions or aqueous, alcoholic or aqueous-alcoholic solutions which contain the N-hydroxybutyl-chitosan in concentrations of 0.1 to 10 percent by weight, preferably from 0.2 to 6 percent by weight.

The auxiliary materials which are generally contained in these cosmetic compositions are, for example, fragrant materials, dyestuffs, preservatives, thickeners, sequestering agents, emulsifiers, sun screen filters and the like.

These preparations for the treatment of the skin particularly take the form of creams or lotions for the care of the hands or the face, or sun screen creams, colored creams, cosmetic milk products for removing makeup, bubble bath and shower preparations or deodorant preparations.

These preparations are produced with the application of classical procedures. For example, in order to form a cream, an aqueous phase, which contains the chitosan derivative, according to the invention, and possibly other components or auxiliary materials in a dissolved state, can be emulsified with an oil phase. Various compounds can be used for the oil phase, for example, paraffin oil, vaseline oil, sweet almond oil, avocado oil, olive oil, fatty acid ester, for example, glyceryl monostearate, ethyl palmitate, and isopropyl palmitate, or alkyl myristates such as propyl myristate, butyl myristate and cetyl myristate. They can also be mixed with fatty acid alcohols, for example, stearyl or cetyl alcohols, or waxes, for example, beeswax or wool wax.

The N-hydroxybutyl-chitosan derivatives can be contained in these cosmetic preparations for the care of the skin and as main active ingredients as well as auxiliary materials.

The new chitosan derivatives contained in the cosmetic compositions, according to the invention, are derived from chitosan, a material which is obtained by deacetylation of chitin, a naturally arising acetyl glucose amine.

The chitosan is insoluble in neutral and alkaline media, but soluble salts are formed on the basis of its chemical nature in an acidic medium with organic and inorganic acids. These soluble salts are used in the paper and textile industries, for example, as additives. Moreover, they are used as coagulants for suspensions, as chelating agents for heavy metal ions, and in medicine and cosmetics (see the publication of Muzarelli: "Chitin", Pergamon Press, 1977).

Several of water-soluble chitosan derivatives are already known, for example, carboxymethyl chitosan (see Nud'ga, Plisko and Danilov, Zhur. Obsh. Khim. 43, No. 12, pages 2752 to 2756 (1973); SU-PS 325 234; and Okimasu, Nippon Nogei Kagaku Kaishi 32, pages 383 to 389 and 471 to 473 (1958)) or sulfoethyl chitosan (see Nud'ga, Plisko and Danilov, Zhur. Prikl. Khim. 47, No. 4, pages 872 to 875 (1974)). However, these water-soluble chitosan derivatives are either changed with respect to their ionic character or are objectionable in a physiological respect.

Hydroxyethyl chitosan (glycol chitosan) was obtained by Senju and Okimasu (Nippon Nogei Kagaku Kaishi 23, pages 423 to 437 (1950)) in the glycolization of chitin in the presence of strong alkalis by means of simultaneous deacetylation.

Because of the low degree of substitution or cross-linkage, water-insoluble hydroxyalkyl derivatives of chitosan, whose strong water-absorbing characteristics are of interest in terms of application technology, are mentioned in JP-PS 54-11 955 of 1979.

Finally, JP-PS 57-180 602 (1982) describes the synthesis of water-soluble chitosan derivatives which are obtained by means of the reaction of alkylene oxides with chitosan in the presence of alkali in a mixture of water and an organic solvent.

All of these more or less water-soluble derivatives are based on the reaction of chitosan with alkylizing agents in the presence of strong alkalis, which results exclusively or predominately in an O-substitution under the selected reaction conditions. However, the presence of alkali, which is necessary for the O-alkylation, determines not only the place of substitution, but also effects a decomposition of the polymer chain, particularly at high temperatures. Moreover, the salts occurring after the reaction by means of neutralizing the excess alkali are by-products which necessitate additional purification steps.

In contrast, DE-OS 32 23 423 and EP-OS 0 097 229 describe water-soluble N-substituted chitosan derivatives which are preferably obtained by means of the reaction of an aqueous dispersion of chitosan with glycide. However, the rapid hydrolysis of the glycide in the presence of water, its high price, and the fact that glycide is not manufactured on an industrial scale makes the process for producing these derivatives more expensive.

If the preferred reaction conditions indicated in DE-OS 32 23 423 are transferred to the reaction of chitosan with butylene oxide, no water-soluble derivatives are obtained.

It has now been found in a surprising manner that chitosan can be reacted with butylene oxide in a simple manner to form hydroxybutyl derivatives with particularly advantageous film and solubility characteristics with the use of mixtures of water and organic solvents.

In the absence of basic catalysts, the substitution of the free amino groups takes place, which is confirmed by determination of the primary amine nitrogen according to van Slyke (see K. H. Bauer and H. Moll, "Die organische Analyse" [Organic Analysis], 2nd edition, pages 170 to 172, Akademische Verlagsgesellschaft Geest und Portig KG, Leipzig 1950, and H. Roth, E. v. Hulle, et al. in "Analytische Methoden" [Analytical Methods], pages 674 to 676, Georg Thieme Verlag, Stuttgart 1953), and by means of $^{13}$C-NMR.

Therefore, the subject matter of the present invention are also water-soluble and alcohol-soluble N-hydroxybutylchitosans derived from chitosan, and their salts with organic or inorganic acids, consisting of (a) 4 to 40 mole percent monomer units of the formula (I)

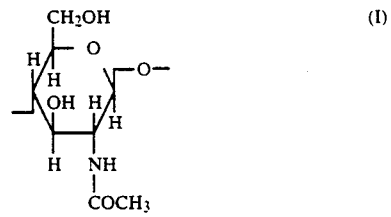

and (b) 60 to 96 mole percent monomer units of the formula (II)

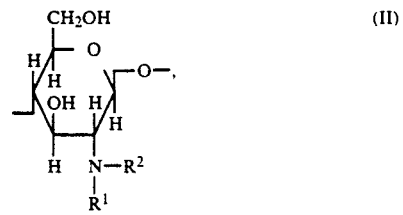

wherein $R^1$ and $R^2$ can be identical or different and designate either hydrogen or the radical of the formula (III):

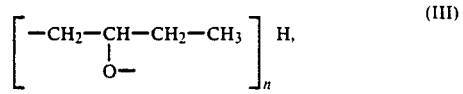

n being equal to an integer from 1 to 5, provided that $R^1$ and $R^2$ do not simultaneously designate hydrogen in at least 50 percent of the units of formula (II).

The new chitosan derivatives are obtained, according to the invention, in that a suspension of chitosan (at 60 to 96 percent deacetylated chitin), or its salts, are converted at temperatures between 20 and 120 degrees Celsius, preferably between 40 and 100 degrees Celsius, under pressure in an autoclave in a suitable ratio with butylene oxide (1,2-epoxy butane) over a period of 3 to 72 hours, preferably 6 to 48 hours.

In a preferred manner, the reaction is carried out in a mixture consisting of water and an organic solvent in a neutral medium. With the use of chitosan salts or chitosan in the presence of acidic catalysts, such as hydrochloric acid, the reaction can be effected in a dispersion or solution consisting of water and an organic solvent or water and excess butylene oxide. The molar ratio of chitosan to butylene oxide is between 1:3 and 1:15.

After the reaction is finished, the excess alkylizing agent is removed, insoluble portions, which may be present, are separated from the solutions of the chitosan derivative by means of filtration, neutralization is possibly carried out, the composition is reduced in a rotary evaporator, and the chitosan derivative precipitates immediately or after dialysis in acetone.

The salts of the N-hydroxybutyl-chitosans, according to the invention, can be obtained by means of neutralization of the amino groups of the N-hydroxybutyl-chitosans with inorganic or organic acids. According to the present invention, however, only those salts which are soluble in water are usable. Suitable salts are, for example, those formed with hydrochloric acid, glycolic acid, lactic acid, formic acid, citric acid or acetic acid.

The following examples will explain the subject matter of the invention in more detail without limiting it to these examples.

PRODUCTION EXAMPLES

Example 1

50 g (0.31 moles) of low-molecular, ground chitosan with a limiting viscosity number (Eta) of 160 ml/g and a degree of deacetylation of 90 percent are dispersed in 200 ml isopropanol/water (1:1) and mixed in an autoclave with 64.9 g (0.9 moles) butylene oxide. After a reaction time of 12 hours at 100 degrees Celsius, the excess alkylizing agent is removed by means of bubbling through nitrogen or by means of briefly heating to boiling under the hood after the highly viscous reaction product has been diluted with isopropanol in a ratio of 1:1.

After pressure filtration for the purpose of removing unreacted portions, the filtrate is reduced in the rotary evaporator and, finally, precipitation is carried out in 8 to 10 times the quantity of acetone.

The precipitated derivative is dispersed by means of an Ultra-Turax in order to remove entrapped butylene glycols.

The precipitate is collected on a glass sintering suction filter, thoroughly washed with acetone and dried at 50 degrees Celsius in a vacuum drying closet.
45 g N-hydroxybutyl-chitosan is obtained.

| Characteristic data | |
|---|---|
| limiting viscosity number (Eta) = | 62 ml/g |
| degree of substitution, hydroxybutyl = | 2.1 |
| pendulum hardness = | 207 sec. |
| moisture vapor absorption = | 5.8 percent |

Example 2

20 g (0.12 moles) of a high-molecular chitosan with a limiting viscosity number (Eta) of 1600 ml/g and a degree of deactylation of 76 percent are dispersed in a pressure vessel in a mixture of 800 ml ethanol/water (1:1), mixed with 77.9 g (1.08 moles) butylene oxide and made to react accompanied by stirring at 80 degrees Celsius for 20 hours. The preparation is effected as described in example 1.
The yield of N-hydroxybutyl-chitosan is 25.4 g.

| | |
|---|---|
| limiting viscosity number (Eta) = | 215 ml/g |
| degree of substitution, hydroxybutyl = | 1.5 |
| pendulum hardness = | 176 sec. |
| moisture vapor absorption = | 7.1 percent |

Example 3

50 g (0.3 moles) of a low-molecular, ground chitosan with a limiting viscosity number (Eta) of 160 ml/g and a deactylation degree of 90 percent are dispersed in a mixture of 100 ml isopropanol 100 ml water, accompanied by the addition of 43.8 g (0.3 moles) 25 percent hydrochloric acid, and reacted in an autoclave with 129.8 g (1.8 moles) butylene oxide for 24 hours at 90 degrees Celsius.

The reaction product is worked up after the neutralization and dialysis as described in example 1.
55 g N-hydroxybutyl-chitosan is obtained.

| Characteristic data | |
|---|---|
| limiting viscosity number (Eta) = | 63 ml/g |
| degree of substitution, hydroxybutyl = | 2.0 |
| pendulum hardness = | 200 sec. |
| moisture vapor absorption = | 4.1 percent |

The degree of substitution for the hydroxybutyl radical was determined by means of the $^1$H-NMR spectrum.

The measurement of the limiting viscosities was effected in an aqueous solution of 0.2 moles/l of acetic acid and 0.1 moles/l sodium acetate (chitosan) or in an aqueous solution of 0.2 moles/l acetic acid and 0.1 moles/l sodium chloride (N-hydroxybutyl-chitosan) at 25 degree Celsius accompanied by the use of a DIN-Ubbelohde viscosimeter.

The pendulum hardness was determined according to König (W. König, "Härtemessungen mit dem Pendelhärteprüfer", [Hardness Measurements with the Pendulum Hardness Tester], Farbe und Lack [Paint and Lacquer] 65, pages 435 to 443 (1959); DIN 53 157).

The water absorption was determined at 70 percent relative humidity as opposed to 30 percent relative humidity.

Examples for cosmetic compositions

Example 4 Hair Spray

| | |
|---|---|
| 3.5 g | N-hydroxybutyl-chitosan according to example 3 (Eta = 63 ml/g, degree of substitution = 2.0) |
| 0.6 g | perfume oil |
| 95.9 g | ethanol (96 percent) |
| 100.0 g | |

Filling ratio:
26.8 percent active ingredient
53.2 percent $FCCl_3$
20.0 percent propane/butane (pressure: 0.27 MPa at 20 degrees Celsius

Example 5 Hair setting composition

| | |
|---|---|
| 0.6 g | N-hydroxybutyl-chitosan according to example 1 (Eta = 62 ml/g, degree of substitution = 2.1) |
| 25.0 g | isopropanol |
| 0.4 g | formic acid (10-percent aqueous solution) |
| 0.2 g | perfume oil |
| 73.8 g | water |
| 100.0 g | |

20 ml of this solution were distributed on washed, towel-dried hair. Next, the hair is set in the conventional manner for the hairstyle and dried. The hair has a more pleasant and softer feel in comparison with a hair setting composition based on chitosan/formic acid, as well as good holding action.

Example 6 Spray drying lotion

| | |
|---|---|
| 0.5 g | N-hydroxybutyl-chitosan according to example 3 (Eta = 63 ml/g, degree of substitution = 2.0) |
| 58.0 g | isopropanol |
| 0.1 g | cetyl trimethyl ammonium chloride |
| 0.4 g | phthalic acid diethyl ester |
| 0.4 g | perfume oil |
| 40.6 g | water |
| 100.0 g | |

Filling ratio:
91 percent active ingredient
9 percent propane/butane (pressure: 0.27 MPa at 20 degrees Celsius)

The hair drying lotion is sprayed on the washed, towel-dried hair. Next, the hair is dried and shaped in the usual way. The hair has a substantially more pleasant and softer feel compared to a drying lotion with synthetic polymers as well as good conditioning.

Example 7 Tinting strengthener

| | |
|---|---|
| 0.60 g | N-hydroxybutyl-chitosan according to example 1 (Eta = 62 ml/g, degree of substitution = 2.1) |
| 0.15 g | 1,4-bis-[(2-hydroxyethyl)-amino]-2-nitro-5-chlorobenzene |
| 45.00 g | ethanol |
| 54.25 g | water |
| 100.00 g | |

20 ml of this solution are put on the washed, towel-dried hair, the hair is then set and dried. The hair is dyed red-violet and set.

Example 8 Anionic hair washing composition

| | |
|---|---|
| 1.00 g | N-hydroxybutyl-chitosan according to example 2 (Eta = 215 ml/g, degree of substitution = 1,5) |
| 40.00 g | lauryl alcohol diglycol ether sulfate sodium salt (28-percent aqueous solution) |
| 4.00 g | sodium chloride |
| 0.05 g | dyestuff |
| 0.10 g | formaldeyde (25-percent aqueous solution) |
| 54.85 g | water |
| 100.00 g | |

A clear shampoo is obtained. The hair which is washed with it is conditioned in an outstanding manner with respect to feel, luster and combing facility

Example 9 Amphoteric, tinting hair washing composition

| | |
|---|---|
| 2.00 g | N-hydroxybutyl-chitosan according to example 1 (Eta = 62 ml/g, degree of substitution = 2.1) |
| 40.00 g | dimethylcarboxy methylene propylene amido-stearate betaine (35-percent aqueous solution) |
| 5.06 g | formic acid (10-percent aqueous solution) |
| 1.00 g | picramic acid (one-percent aqueous solution) |
| 3.50 g | coconut fatty acid (one-percent aqueous solution) |
| 48.44 g | water, deionized |
| 100.00 g | |

15 to 20 g of the above hair washing composition are shampooed into the hair. After allowing it to act for a period of 5 to 10 minutes, the hair is rinsed with water. The hair is tinted a yellow-orange color and conditioned in an excellent manner.

Example 10 Cationic hair treatment composition

| | |
|---|---|
| 0.30 g | N-hydroxybutyl-chitosan according to example 2 (Eta = 215 ml/g, degree of substitution = 1.5) |
| 4.00 g | cetyl stearyl alcohol |
| 1.48 g | lactic acid (10-percent aqueous solution) |
| 2.50 g | coconut(pentaethoxy)methyl ammonium chloride |
| 1.00 g | sorbitanmonopalmitate, ethoxylated with 20 moles ethylene oxide |
| 90.72 g | water, deionized |
| 100.00 g | |

35 g of the hair treatment composition in accordance with example 10 is distributed on the washed hair and after being allowed to act for 3 to 5 minutes is rinsed out again with water. An excellent feel, luster and combing ability of the hair result.

Example 11 Hair treatment composition, gel form

| | |
|---|---|
| 2.1 g | N-hydroxybutyl-chitosan according to example 2 (Eta = 215 ml/g, degree of substitution = 1.5) |
| 0.6 g | hydroxypropylmethyl cellulose |
| 0.5 g | lauryl pyridinium chloride |
| 96.8 g | water, deionized |
| 100.00 | (adjusted to pH 5.0 with ten-percent formic acid) |

The gel is used in the same way as in example 9. The feel, luster and combing ability of the hair is substantially improved as a result.

Example 12 Hair tinting composition

| | |
|---|---|
| 0.30 g | N-hydroxybutyl-chitosan according to example 1 (Eta = 62 ml/g, degree of substitution = 2.1) |
| 12.00 g | cetyl stearyl alcohol |
| 0.10 g | 4-hydroxy-benzoic acid ethyl ester |
| 6.00 g | lauryl alcohol diglycolic ether sulfate sodium salt (28-percent aqueous solution) |
| 0.50 g | perfume oil |
| 0.50 g | 1-hydroxy-2-amino-4-nitrobenzene |
| 0.85 g | 1,4-diamino-2-nitrobenzene |
| 0.24 g | sodium hydroxide |
| 79.51 g | water |
| 100.00 g | |

30 to 40 g of the aforementioned hair tinting composition are distributed on washed hair and, after being allowed to act for approximately 20 minutes, are rinsed out. The hair is dyed a reddish color and has a good combing ability and a pleasant feel.

Example 13 Oxidizing hair dye composition

| | |
|---|---|
| 0.50 g | N-hydroxybutyl-chitosan according to example 2 (Eta = 215 ml/g, degree of substitution = 1.5) |
| 0.08 g | 3,5-diamino-2,6-dimethoxypyridine dihydrochloride |
| 0.30 g | 1,4-diaminobenzene |
| 0.25 g | resorcinol |
| 0.30 g | sodium sulfite |
| 3.50 g | lauryl alcohol diglycol ether sulfate sodium salt (28-percent aqueous solution) |
| 15.00 g | cetyl alcohol |
| 3.00 g | ammonia |
| 77.07 g | water |
| 100.00 g | |

50 g of this hair dye composition are mixed with 50 ml 6-percent hydrogen peroxide solution and applied to white hair. After 30 minutes, the hair is rinsed with water and dried. The hair has obtained a naturally acting dull-blond coloring and a natural, pleasant feel.

Example 14 Permanent wave composition

| | |
|---|---|
| 0.5 g | N-hydroxybutyl-chitosan according to example 3 (Eta = 63 ml/g, degree of substitution = 2,0) |
| 10.0 g | thioglycolic acid |
| 8.0 g | ammonia (25-percent aqueous solution) |
| 6.1 g | ammonium hydrogen carbonate |
| 75.4 g | water |
| 100.00 g | |

To use, this permanent wave composition is uniformly applied to towel-dried hair, which is wound in curlers, and is allowed to act for approximately 20 minutes. Next, the hair is rinsed with water and treated oxidatively in a known manner. A good wave result is obtained and the hair feels natural and soft to the touch.

Example 15 Skin cream

| | |
|---|---|
| 0.30 g | N-hydroxybutyl-chitosan according to example 1 (Eta = 62 ml/g, degree of substitution = 2.1) |
| 3.00 g | stearyl alcohol |
| 1.00 g | wool wax (adeps lanae) |
| 1.00 g | petrolatum |
| 0.76 g | lactic acid (10-percent aqueous solution) |
| 1.00 g | sodium acetyl stearyl sulfate |
| 92.94 g | water |
| 100.00 g | |

All percentages given in the present application are percent by weight.

While the invention has been illustrated and described as embodied in cosmetic compositions based upon N-hydroxybutyl chitosans, new N-hydroxybutyl chitosans and processes for making same, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

We claim:

1. Cosmetic composition for treatment of hair or skin comprising as active ingredient an effective amount of a chitosan derivative selected from the group consisting of N-hydroxybutylchitosans, consisting of (a) 4 to 40 mole percent monomer units of formula (I)

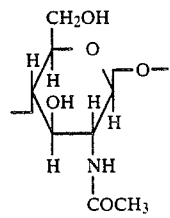

and (b) 60 to 96 mole percent monomer units of the formula (II)

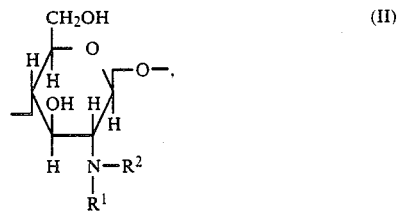

wherein $R^1$ and $R^2$ are each independently selected from the group consisting of a hydrogen atom and radicals of the formula (III)

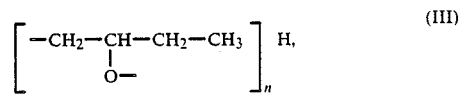

with n being equal to an integer from 1 to 5, provided that $R^1$ and $R^2$ are not simultaneously hydrogen in at least 50 percent of the monomer units of formula (II), and soluble salts thereof; and provided in a form selected from the group consisting of an aqueous preparation, alcoholic preparations and aqueous-alcoholic preparations.

2. Composition according to claim 1, containing said N-hydroxybutyl chitosan in an amount of 0.5 to 10.0 percent by weight.

3. Composition according to claim 1, provided in a form selected from the group consisting of solutions, creams, gels, dispersions and emulsions.

4. Composition according to claim 1, having a pH value from 2 to 11.

5. Composition according to claim 1, further comprising a film-forming cosmetic polymer, which is selected from the group consisting of shellac, alginates, gelatines, pectins, cellulose derivatives, polyvinylpyrrolidone, polyvinyl acetate, acrylic acid polymers, methacrylic acid polymers, basic polymers of esters from acrylic acid with amino alcohols, basic polymers of esters from methacrylic acid with amino alcohols, salts of said basic polymers, quaternization products of said basic polymers, polyacrylonitrile and polyvinylpyrrolidone-vinyl acetate.

6. Composition according to claim 1, further comprising at least one cosmetic dyestuff in a concentration of 0.01 to 2.0 percent by weight and provided in the form of a dyeing or tinting strengthener.

7. Composition according to claim 1, further comprising an intermixed propellant liquified under pressure, said composition being fillable into a pressurized container for subsequent production of an aerosol spray or an aerosol foam.

8. Composition according to claim 1, further comprising at least one surfactant selected from the group consisting of cationic, nonionic, amphoteric and anionic surface-active agents and provided in the form of a hair washing composition.

9. Composition according to claim 8, containing said surfactant in a concentration of 3 to 50 percent by weight and having a pH value between 3 and 9.

10. A macromolecular N-hydroxybutylchitosan, comprising
(a) 4 to 40 mole percent monomer units of the formula (I)

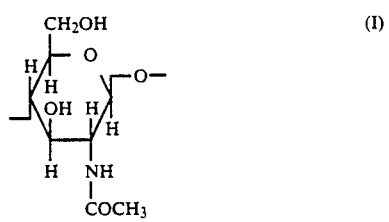

(b) 60 to 96 percent monomer units of the formula (II)

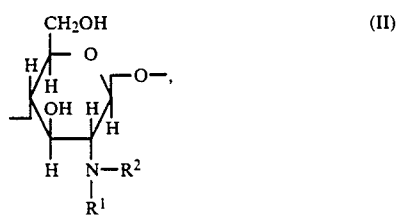

wherein $R^1$ and $R^2$ are each independently selected from the group consisting of a hydrogen atom and radicals of the formula (III),

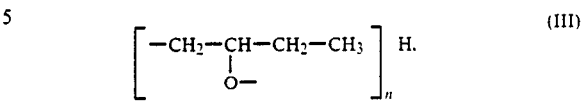

with n being equal to an integer from 1 to 5, provided that $R^1$ and $R^2$ are not simultaneously hydrogen in at least 50 percent of the monomer units of formula (II), and soluble salts thereof with acids.

11. Process for producing a macromolecular N-hydroxybutylchitosan according to claim 10, comprising reacting a chitosan reactant selected from the group consisting of 60 to 96 percent deacetylated chitins and salts thereof for 3 to 72 hours at a temperature of 20° to 120° C. with butylene oxide in a ratio of from 1:3 to 1:15.

12. Process according to claim 11, wherein said reacting of said chitosan reactant consisting of said 60 to 96 percent deacetylated chitin with said butylene oxide occurs in a mixture comprising water and an organic solvent in neutral medium.

13. Process according to claim 11, wherein said chitosan reactant is reacted in the presence of an acid catalyst in a dispersion selected from the group consisting of dispersions of water and organic solvents and dispersions of water and excess butylene oxide.

14. Process according to claim 11, wherein said chitosan reactant is reacted in the presence of an acid catalyst in a solution selected from the group consisting of solutions of water and organic solvents and solutions of water and excess butylene oxide.

* * * * *